US012758606B2

(12) United States Patent
Novellino et al.

(10) Patent No.: US 12,758,606 B2
(45) Date of Patent: Oct. 13, 2026

(54) FOOD SUPPLEMENT TO PROMOTE BODY WEIGHT LOSS

(71) Applicant: NGN HEALTHCARE—NEW GENERATION NUTRACEUTICALS S.R.L., Mercogliano (IT)

(72) Inventors: Ettore Novellino, Avellino (IT); Gian Carlo Tenore, Naples (IT)

(73) Assignee: NGN Healthcare-New Generation Nutraceuticals S.R.L., Mercogliano (IT)

( * ) Notice: Subject to any disclaimer, the term of this patent is extended or adjusted under 35 U.S.C. 154(b) by 318 days.

(21) Appl. No.: 18/280,508

(22) PCT Filed: Mar. 8, 2022

(86) PCT No.: PCT/IB2022/052027

§ 371 (c)(1),
(2) Date: Sep. 6, 2023

(87) PCT Pub. No.: WO2022/189952

PCT Pub. Date: Sep. 15, 2022

(65) Prior Publication Data

US 2024/0148815 A1 May 9, 2024

(30) Foreign Application Priority Data

Mar. 9, 2021 (IT) ........................ 102021000005429

(51) Int. Cl.

| | |
|---|---|
| ***A61K 36/74*** | (2006.01) |
| ***A61K 9/19*** | (2006.01) |
| ***A61K 9/48*** | (2006.01) |
| ***A61K 31/365*** | (2006.01) |
| ***A61K 31/405*** | (2006.01) |
| ***A61K 31/49*** | (2006.01) |
| ***A61K 31/7048*** | (2006.01) |
| ***A61K 36/28*** | (2006.01) |
| ***A61K 36/48*** | (2006.01) |
| ***A61K 36/515*** | (2006.01) |
| ***A61P 3/04*** | (2006.01) |

(52) U.S. Cl.

CPC ................ *A61K 36/74* (2013.01); *A61K 9/19* (2013.01); *A61K 9/485* (2013.01); *A61K 9/4866* (2013.01); *A61K 31/365* (2013.01); *A61K 31/405* (2013.01); *A61K 31/49* (2013.01); *A61K 31/7048* (2013.01); *A61K 36/28* (2013.01); *A61K 36/48* (2013.01); *A61K 36/515* (2013.01); *A61P 3/04* (2018.01)

(58) Field of Classification Search

None

See application file for complete search history.

(56) References Cited

U.S. PATENT DOCUMENTS

| | | | | |
|---|---|---|---|---|
| 5,006,338 A * | 4/1991 | Luenemann ........... | A61K 36/11 514/885 |
| 2009/0258896 A1 | 10/2009 | Jain et al. | |
| 2014/0030332 A1 | 1/2014 | Baron et al. | |

FOREIGN PATENT DOCUMENTS

| | | |
|---|---|---|
| WO | 2005016018 A2 | 2/2005 |

OTHER PUBLICATIONS

Versini (FR 2622453—English translation)—1989.*
Cettour-Rose (BMC Physiology (2013), col. 13, No. 5, 11 pages).*
De Kraker (Plant Physiol. (1998), vol. 117, pp. 1381-1392).*
Lee (KR 20190087149 (Jul. 24, 2019)—English translation).*
McHugh ("Freeze-Drying Fundamentals." Food Technology Magazine (2018), 13 pages, accessed at https://www.ift.org/news-and-publications/food-technology-magazine/issues/2018/february/columns/processing-freeze-drying-foods).*
Park (KR 20190125804 (Nov. 7, 2019)—English translation).*
Wang (Cells (Jan. 2020), vol. 9, No. 331, 15 pages).*
Andreozzi, P. , et al., "The Bitter Taste Receptor Agonist Quinine Reduces Calorie Intake and Increases the Postprandial Release of Cholecystokinin in Healthy Subjects", J Neurogastroenterol Motil, 21(4)http://dx.doi.org/10.5056/jnm15028, 511-519, 2015.
Belitz, H-D. , et al., "Bitter Compounds: Occurrence And Structure—Activity Relationships", Food Reviews Intl., 1(2), 271-354, 1985.
Foure, M. , et al., "Chicory Roots for Prebiotics and Appetite Regulation: A Pilot Study in Mice", J. Agric. Food Chem., 66, 6439-6449, 2018.
Janssen, S. , et al., "Bitter taste receptors and α-gustducin regulate the secretion of ghrelin with functional effects on food intake and gastric emptying", PNAS, 108(5)www.pnas.org/cgi/doi/10.1073/pnas.1011508108, 2094-2099, 2011.
Mennella, I. , et al., "Microencapsulated bitter compounds (from *Gentiana lutea*) reduce daily energy intakes in humans", Brit J Nutri., 116doi:10.1017/S0007114516003858, 1841-1850, 2016.

* cited by examiner

*Primary Examiner* — Susan Hoffman
(74) *Attorney, Agent, or Firm* — Elmore Patent Law Group, P.C.; Joseph C. Zucchero; Carolyn S. Elmore

(57) ABSTRACT

The present invention describes a gastro-resistant pharmaceutical/nutraceutical composition comprising chincona cortex freeze-dried (*Cinchona succirubra*), chicory leaves and roots freeze-dried (*Cichorium intybus*, and/or *Cichorium endivia*, and/or *Cichorium pumilum*, and/or *Cichorium spinosum*), and gentian root freeze-dried (*Gentiana lutea*), and optionally *griffonia* seed extract (*Griffonia simplicifolia*). The nutraceutical composition object of the present invention is useful for appetite control, mealtime energy intake reduction, and body weight loss.

15 Claims, No Drawings

FOOD SUPPLEMENT TO PROMOTE BODY WEIGHT LOSS

FIELD OF THE INVENTION

The present invention relates to the field of food supplements, in particular food supplements suitable for promoting body weight loss.

STATE OF THE ART

Obesity is a chronic disease spread all over the world, capable of increasing the risk factors for many pathological conditions, such as cardiovascular diseases, hypertension, infertility, diabetes mellitus, and dyslipidemia. The World Health Organization (WHO) has defined obesity as an abnormal or excessive fat accumulation that may impair health and is indicated by a body mass index (BMI) 30 $kg/m^2$. Obesity has a multifactorial etiology: it involves, in fact, genetic and hormonal factors, as well as social and environmental factors, mainly represented by a sedentary lifestyle and bad eating habits. Previous studies have shown that a weight loss of 5-10% in people with obesity associated with other comorbidities can significantly improve health and counteract mortality due to many obesity-associated diseases. A rich scientific literature indicates that a healthy diet and an active lifestyle play a key role in the prevention and treatment of obesity. However, to date, the common interest is to find a supportive treatment that can fight or prevent obesity and promote and protect individual health.

The past few decades have witnessed the conceptual evolution of the gastrointestinal tract, from being solely a site of nutrients digestion and absorption, to its recognition as the largest endocrine system in the body. More than 30 peptides are known to be released from enteroendocrine cells within the gastrointestinal mucosa. These gut-derived hormones communicate with tissues both inside and outside the gut and play a pivotal role in the regulation of metabolic homeostasis. Of particular importance are ghrelin, released from the enteroendocrine Gr-cells (in the stomach); cholecystokinin (CCK), from I-cells (mainly in the upper small intestine); glucose-dependent insulinotropic polypeptide (GIP), from K-cells (largely in the upper small intestine); glucagon-like peptide-1 (GLP-1) and YY peptide (PYY), from L-cells (predominantly in the distal small and large intestine). Ghrelin is mainly secreted during fasting and is subsequently suppressed after meals. It is regarded as the "hunger" hormone, that regulates food intake and accelerates gastric emptying. Conversely, CCK, GIP, GLP-1 and PYY are predominantly released after the meals and, in concert, mediate intestinal feedback to limit postprandial glycemic excursions and reduce energy intake. In recognition of the pleiotropic actions of gastrointestinal hormones in the regulation of metabolic homeostasis, various synthetic drugs, especially GLP-1 receptor agonists and GLP-1/GIP double agonists are experiencing a rapid development by the pharmaceutical industry, to better manage obesity and related metabolic diseases. This approach, however, is often limited by cost, side effects (mainly gastrointestinal symptoms) and suboptimal efficacy (particularly for obesity). Dietary strategies to modulate endogenous secretion of gastrointestinal hormones represent an alternative that shows substantial promise. For example, consuming a "preload" of nutrients before the main meal has been shown to reduce postprandial blood sugar by stimulating GLP-1 secretion before the meal and slowing gastric emptying. However, this approach requires additional energy associated with the preload.

Recent scientific literature describes preclinical and clinical models that support a functional link between gastrointestinal bitter taste receptors (BTRs) and gastrointestinal hormone secretion. These results indicate that the stimulation of BTRs by bitter-tasting substances may be exploited to modulate gastrointestinal motility and energy intake in humans. The gastrointestinal modulation of hormone secretion by compounds with low or no caloric intake, such as bitter-tasting substances, would therefore be advantageous compared to synthetic drugs and nutrient preloading. Some examples are reported below.

Studies in mice have shown that intragastric administration of a mixture of BTRs agonists, such as, denatonium benzoate (DB), phenylthiocarbamide (PTC), quinine and D-[-] salicin, may favor an increase in plasma ghrelin levels, associated to a transient increase in food intake during the first 30 minutes, followed by prolonged intake suppression over the next 4 h (Janssen S, et al. Proc. Natl. Acad. Sci. USA, 2011, 108: 2094-9).

A clinical intervention study conducted on young healthy subjects showed that oral administration of encapsulated quinine HCl (18 mg) resulted in increased CCK plasma concentrations and reduced energy intake during an ad libitum meal (Andreozzi P, et al. J. Neurogastroenterol. Motil. 2015, 21:511-9). Furthermore, in this study, the extent of energy intake suppression in response to quinine HCl was directly related to the subjects' sensitivity to the bitter taste of PTC.

In vitro studies have shown that numerous bitter compounds are able to induce of GLP-1 secretion from enteroendocrine cells, through interaction with BTRs. For example, berberine, a naturally occurring bitter alkaloid of plant origin, and phenylthiourea, have been shown to dose-dependently stimulate GLP-1 secretion in NCI-716 and STC-1 cells by interacting with T2R38. In rodents, intestinal exposure to BTRs agonists was found to increase GLP-1 plasma levels. In particular, an intragastric preload of DB, prior to the administration of enteral glucose, resulted in an increase in GLP-1 plasma levels and insulin concentration, a slowing of gastric emptying, and a reduction in blood glucose. Long-term intragastric administration (4 weeks) of DB confirmed the effect of an increase in meal-induced GLP-1 secretion, associated with a body weight reduction in obese mice. A clinical study in healthy subjects evaluated the effect of a single low-dose of encapsulated dry extract of *Gentiana lutea* root on the release of GLP-1 in the small intestine and observed the trend towards a higher response in case of a standard breakfast, and a reduction in post-prandial energy intake, compared to placebo.

Information regarding the effect of BTRs agonists on the secretion of PYY released by L cells is limited. Although DB stimulates PYY secretion from NCI-H716 cells, in a similar way to GLP-1 (20), this effect has not so far been evaluated in vivo.

These data indicate that the stimulation of intestinal BTRs by bitter substances can be exploited to modulate gastrointestinal functions, decrease energy intake, and promote body weight loss, with positive clinical implications for the management of obesity and related dysmetabolic diseases.

In this regard, there are numerous evidence in the scientific literature indicating many natural substances with a bitter taste capable of contributing to the gastrointestinal modulation of hormone secretion by interaction with BTRs.

As previously reported, oral administration of encapsulated formulations based on *cinchona* cortex alkaloids, in particular encapsulated quinine HCl (Janssen S, et al., 2011; Andreozzi P, et al., 2015), and of secoiridoid glycosides of Gentian (*Gentiana lutea*) root, such as gentiopicrin (Mennella I, et al., Br. J. Nutr. 2016, 116: 1-10), favored the increase in plasma concentrations of gastrointestinal hormones, such as CCK and GLP-1, reducing mealtime energy intake in healthy subjects (Janssen S, et al., 2011; Andreozzi P, et al., 2015).

Sesquiterpene lactones, typical constituents with a strong bitter taste, present in the roots and leaves of numerous species of chicory (*Cichorium*), have also shown the ability to reduce appetite and the consequent mealtime caloric intake. A 5-week pilot dietary intervention study, conducted in mice, demonstrated that various extracts of chicory (*Cichorium intybus*) roots, rich in lactucin and lactucopicrin, are strongly able to control appetite, through substantial changes in the release of satiety hormones and in the composition of the intestinal microbiota. In particular, there was a significant increase in the plasma concentration of CCK and GLP-1 gastrointestinal hormones (Marion Fouréet al., J. Agric. Food Chem. 2018, 66, 6439-6449).

Currently, an important field of research concerns food supplements that contain molecules capable of controlling appetite sensation. These appetite modulators include tryptophan, as it is a precursor to the neurotransmitter serotonin. Tryptophan consumed as part of the diet is carried into the cells, where it undergoes enzymatic hydroxylation with the formation of 5-hydroxytryptophan (5-HTP). Subsequently, a decarboxylation process takes place with the production of 5-hydroxytryptamine (5-HT) (serotonin). Serotonin is a monoamine neurotransmitter synthesized within the serotonergic neurons of the central nervous system, as well as within the enterochromaffin cells of the gastrointestinal system. Serotonin is considered a modulatory neurotransmitter within the central nervous system, with inhibitory effects on appetite. Plasma concentrations of tryptophan are reported to be low in obese subjects, both when measured at single time points, although not always, and over a 24-hour period. Furthermore, plasma tryptophan remains low after weight loss and decreases with diet, an effect that may be partly responsible for the high relapse rate after diet-related weight loss. The role of amino acids in regulating food intake has been supported by experimental data suggesting that changes in amino acid plasma concentrations can modify food intake by affecting the brain availability of neurotransmitter amino acid precursors. Previous observations have shown that oral administration of 5-HTP is beneficial for weight loss. A randomized, double-blind, placebo-controlled study was conducted on 20 overweight women. These subjects were randomly assigned to supplement their diet with *Griffonia simplicifolia* seed extract with high concentration (99%) of 5-HTP (10 subjects) or a placebo (10 matched subjects), for 4 weeks, in combination with a personalized, calorie-reduced diet. Primary endpoints were the appetite sensation assessment (by Haber score), body composition and amount of food consumed. Supplementing the diet of overweight women with 5-hydroxytryptophan significantly increased the feeling of satiety associated with a decrease in BMI.

The object of the present invention is to provide a nutraceutical composition which can be at least a useful alternative for contributing to body weight loss.

SUMMARY OF THE INVENTION

The object of the present invention is a gastro-resistant pharmaceutical/nutraceutical composition comprising chincona cortex freeze-dried (preferably of *Cinchona succirubra*), chicory leaves and roots freeze-dried (preferably of *Cichorium intybus*, and/or *Cichorium endivia, e*/o *Cichorium pumilum*, and/or *Cichorium spinosum*) and gentian root freeze-dried (preferably of *Gentiana lutea*).

The nutraceutical composition object of the present invention is useful for appetite control and/or mealtime energy intake reduction and/or body weight loss.

DETAILED DESCRIPTION OF THE INVENTION

It was surprisingly found that the combination of these components produces a synergistic effect in decreasing body weight.

Preferably, the composition of the invention further comprises *griffonia* seeds extract (preferably of *Griffonia simplicifolia*).

Preferably, a composition according to the invention comprises:

| | |
|---|---|
| Chincona cortex freeze-dried | 25-40%; more preferably 30-35%; |
| Chicory leaves and roots freeze-dried | 25-40%; more preferably 30-35%; |
| Gentian root freeze-dried | 25-40%; more preferably 30-35%; |

where the percentages indicated are expressed by weight calculated with respect to the total weight of the composition.

In the composition according to the present invention, the three components, chincona cortex freeze-dried, chicory leaves and roots freeze-dried, and gentian root freeze-dried, are preferably contained in a weight ratio of 1:1:1.

Preferably, in accordance with a second embodiment, a composition according to the invention comprises:

| | |
|---|---|
| Chincona cortex freeze-dried | 25-40%; more preferably 30-35%; |
| Chicory leaves and roots freeze-dried | 25-40%; more preferably 30-35%; |
| Gentian root freeze-dried | 25-40%; more preferably 30-35%; |
| Griffonia seeds extract | 2-15%; more preferably 5-10%; |

where the percentages indicated are expressed by weight calculated with respect to the total weight of the composition.

In the second embodiment, of the composition according to the present invention, the four components, chincona cortex freeze-dried, chicory leaves and roots freeze-dried, gentian root freeze-dried, and *griffonia* seeds extract, are contained in a weight ratio of 1:1:1:0.15.

The composition will normally be formulated in gastro-resistant capsules or tablets, using known techniques (encapsulation, compression, controlled release, microgranules, nanocapsules, multilayer) as described in the pharmacopoeia for the preparation of pharmaceutical formulations for oral use.

A particular example of a pharmaceutical formulation according to the invention consists of gastro-resistant capsules containing:

100-300 mg of chincona cortex freeze-dried, preferably 200 mg;

100-300 mg of chicory leaves and roots freeze-dried, preferably 200 mg;

100-300 mg of gentian root freeze-dried, preferably 200 mg;

optionally 10-50 mg of *griffonia* seeds extract, preferably 30 mg.

Particularly preferably, the composition may contain:

| | |
|---|---|
| quinine | 1-9 mg, preferably 6 mg; |
| lactucin | 0.35-1.05 mcg, preferably 0.70 mcg; |
| gentiopicrin | 2-6, preferably 4 mg; |
| optionally 5-HTP | 9.8-49 mg, preferably 29.4 mg. |

A particular example of a pharmaceutical formulation according to the invention is a gastro-resistant capsule consisting of:

chincona cortex freeze-dried, 200 mg; chicory leaves and roots freeze-dried, 200 mg; gentian root freeze-dried, 200 g. In particular, the composition preferably comprises quinine, 6 mg; lactucin, 0.70 mg; gentiopicrin, 4 mg; and optionally 5-HTP, 29.4 mg.

The composition according to the invention is obtained simply by mixing the components in the required amounts using normal mixers.

The present invention can be better understood in the light of the following embodiments.

EXPERIMENTAL PART

Example 1—Preparation of Chincona Cortex Freeze-Dried

The chincona cortex was subjected to freezing at −50 −80° C., freeze-drying, and grinding.

| | |
|---|---|
| Chincona cortex | 1-3% quinine |

Example 2—Preparation of Chicory Leaves and Roots Freeze-Dried

The chicory leaves and roots were subjected to freezing at −50 −80° C., freeze-drying, and grinding.

| | |
|---|---|
| Chicory leaves freeze-dried | max 350 mg/kg lactucin |

Example 3—Preparation of Gentian Root Freeze-Dried

The gentian root was subjected to freezing at −50 −80° C., freeze-drying, and grinding.

| | |
|---|---|
| Gentian root powder | 1-2% gentiopicrin |

Example 4—Preparation of *Griffonia* Seeds Extract

*Griffonia* seeds were subjected to grinding and subsequent extraction with 95% ethyl alcohol. The alcoholic extract was separated by centrifugation and dried by spray-drying method.

| | |
|---|---|
| Griffonia seeds dry extract | 98% 5-HTP |

Example 5—Preparation of Gastro-Resistant Capsules a. First Embodiment of the Invention (Mix1)

800 mg gastro-resistant capsules, whose heads and bodies consists of 1.9% titanium dioxide, 5.0% gellan gum, hypromellose q.s. to 100%, were selected. A mixture consisting of freeze-dried and excipients (titanium dioxide 5 mg, corn starch 50 mg, microcrystalline cellulose 30 mg, calcium phosphate 5 mg, talc 5 mg, aluminium silicate 5 m), was prepared to fill the capsules so as to ensure an overall content as follows: chincona cortex freeze-dried, 200 mg; chicory leaves and roots freeze-dried, 200 mg; gentian root freeze-dried, 200 mg. In particular, the composition preferably comprises quinine, 6 mg; lactucin, 0.70 mg; gentiopicrin, 4 mg.

b. Second Embodiment of the Invention (Mix2)

800 mg gastro-resistant capsules, whose heads and bodies consists of 1.9% titanium dioxide, 5.0% gellan gum, hypromellose q.s. to 100%, were selected. A mixture consisting of freeze-dried and excipients (titanium dioxide 5 mg, corn starch 50 mg, microcrystalline cellulose 30 mg, calcium phosphate 5 mg, talc 5 mg, aluminium silicate 5 m), in appropriate proportions, was prepared to fill the capsules so as to ensure an overall content as follows: chincona cortex freeze-dried, 200 mg; chicory leaves and roots freeze-dried, 200 mg; gentian root freeze-dried, 200 mg; *griffonia* seeds extract, 30 mg. In particular, the composition preferably comprises quinine, 6 mg; lactucin, 0.70 mg; gentiopicrin, 4 mg; 5-HTP, 29.4 mg.

Example 6—Clinical Data

Study groups. 126 obese subjects, of both sexes, with a Body Mass Index (BMI)≥30 kg/m$^2$ in baseline conditions were recruited at the "Ambulatorio del Programma Dipartimentale "Terapia dietetica nei trapianti e nell'insufficienza renale cronica", Facoltà di Medicina Università Federico II", Naples. The subjects were randomized into 7 groups (18 patients each). Each group was treated with a low-calorie diet for 2 months, plus supplementation, as follows: Group 1, placebo, Group 2, chincona cortex freeze-dried; Group 3, gentian root freeze-dried; Group 4, chicory leaves and roots freeze-dried; Group 5, mix of the three freeze-drieds (mix1); Group 6*, griffonia* seeds extract; Group 7, mixture of the four components (mix2). Patients with diseases such as cancer, acute and chronic metabolic and inflammatory diseases, type 1 and type 2 diabetes treated with insulin and/or hypoglycemic drugs or treated with weight-loss drugs or hormone therapy were excluded. The study was approved by the "Comitato Etico Istituzionale dell'Universitàdegli Studi di Napoli Federico II"; all patients gave their informed consent to the recruitment.

Dietary treatment. A personalized diet plan was set up for each patient of each group, with a 40% caloric restriction of the total energy requirement and the following nutrient composition, in accordance with the RNI (Recommended Nutrient Intake) guidelines: 55-60% of the total caloric intake from carbohydrates, 10-15% from proteins and 20-25% from fatty acids (<7% from saturated fat).

Supplementation. The subjects received a specific treatment, based on the group they belonged to, as follows: Group 1, 600 mg (two capsules)/die of placebo (maltodextrins); Group 2, 600 mg (two capsules)/die of chincona cortex freeze-dried; Group 3, 600 mg (two capsules)/die of gentian root freeze-dried; Group 4, 600 mg (two capsules)/die of chicory leaves and roots freeze-dried; Group 5, 600 mg (two capsules)/die of mixture (mix) of the three freeze-drieds (1:1:1); Group 6, 600 mg (two capsules)/die of *griffonia* seeds extract; Group 7, 630 mg (two capsules)/die of mixture (mix2) of the four components in a ratio of 1:1:1:0.15. The treatment was taken one hour before the main meals. Participants who did not take the treatment for two or more days were excluded from the study. Each patient received the right amount of treatment, provided by the NutraPharmaLabs Laboratories of the "Dipartimento di Farmacia dell'Università degli Studi di Napoli Federico II", to be used for the entire duration of the study.

Study protocol. The subjects were evaluated at the time of recruitment (time TO), after 30 (time T1) and 60 (time T2) days of treatment, using standardized protocols. The nutritional status was assessed by anthropometric measurements: weight (Seca GmbH & Co KG, Hamburg, Germany), height (wall stadiometer with 0.1 cm accuracy), body mass index (BMI), waist circumference (WC), hip circumference (HC). To assess body composition, bioelectrical impedance analysis (BIA) was performed with a four-pole BI (RJL 101; Akern SRL, Florence, Italy). BIA was performed with a single frequency measurement (50 kHz). Visceral adipose tissue (VAT) and subcutaneous adipose tissue (SAT) were evaluated in fasted subjects by the same operator with the Bodymetrix BX2000 instrument. In particular, VAT and SAT were measured 1 cm above the umbilicus at the end of exhalation and applying the same probe pressure for all subjects. Each measurement was performed 3 times and the average of the 3 measurements was used for the analysis. Hand muscle strength (kgm) was measured on dominant and non-dominant hands to the nearest kilogram, using a hand dynamometer (78010; Lafayette Instrument Company, Lafayette, IN, USA). During the measurement, the participant was standing, and the arm of the measured hand was unsupported and parallel to the body. Indirect calorimetry was performed in measuring energy expenditure to assess the energy needs, using the VMAX 2900 calorimeter. In particular, the calorimeter uses the amount of inspired and expired gas exchanges to calculate energy expenditure. The canopy system was used during the test with no compression mask in order to use a light and comfortable device without pressure or contact with the subject's face. The participant was placed in the supine position, free from physical and psychological stress, fasted and awake.

Compliance. Compliance with the dietary intervention was assessed with the aid of Food Frequency Questionnaires, monitoring food intake at baseline and every month, until the end of the study. Assessment of compliance with physical activity was verified by asking subjects to complete a physical activity questionnaire. Compliance with the supplements was assessed by means of a daily questionnaire that asked each volunteer how long the supplement was consumed, as well as assessing the presence of adverse events.

Statistical Analysis

Randomization

A total of 126 eligible patients (67 men and 59 women) were randomly assigned to 7 subgroups (18 subjects each). If a patient left the group before the intervention period, he would be replaced by the next eligible patient enrolled. Concealed allocation was performed by an Internet-based randomization program, stratified by study site. The list of random numbers was generated by an investigator with no clinical involvement in the study. Patients, doctors, laboratory technicians and trial staff (data analyst statisticians) were unaware of the treatment assignment.

Primary and Secondary Efficacy Outcomes

The primary endpoints measured were changes in body weight (BW) and body mass index (BMI). The secondary endpoints measured were changes in fat mass (FM) and lean mass (FFM). All considerations relating to untreated patient were blindly assessed at the main investigation site.

The decision-making process was performed based on a consensus document (unpublished standard operating procedure).

Safety

Safety was determined by adverse event reports, laboratory parameters regarding liver and kidney function, vital signs (blood pressure, pulse, height, weight, and body mass index), physical and neurological examinations. Safety was assessed for the entire treatment period on days 8, 35, 55 and 80, including adverse events occurring in the first three weeks after cessation of treatment.

Power-Analysis

For proportion analysis, the effect size is estimated from the relative risk RR frequencies between the two experimental groups (e.g., in the primary study RR corresponds to the probability of receiving a drug treatment/probability of not receiving it). Since there are no previous studies similar to this one available, the effect size estimates were conducted assuming the following scenarios:

Risk in the placebo group: 99%, 90%, 80%

Risk in the treatment groups: 70%, 50%, 30%

The resulting RR used to estimate the sample size are:

| | 99% | 90% | 80% |
|---|---|---|---|
| 70% | 1.41 | 1.28 | 1.14 |
| 50% | 1.98 | 1.80 | 1.60 |
| 30% | 3.30 | 3.00 | 2.67 |

This indicates that the sample size estimates explore situations where the risk of receiving drug treatment in treated patients is from about 1.1 to 3.3 times lower than in the control.

The sample size calculations were performed with three 1-β power values equal to 0.80, 0.95 and 0.99, and significance level α=0.05.

The following table shows the overall sample sizes for the various hypotheses formulated.

| Risk in the placebo group | Risk in the treatment groups | RR (placebo/treatment) | (1-β) = 0.99 α = 0.05 | (1-β) = 0.95 α = 0.05 | (1-β) = 0.80 α = 0.05 |
|---|---|---|---|---|---|
| 99% | 30% | 3.30 | 30 | 24 | 18 |
| | 50% | 1.98 | 56 | 44 | 30 |
| | 70% | 1.41 | 118 | 88 | 60 |
| 90% | 30% | 3.00 | 46 | 36 | 26 |
| | 50% | 1.80 | 96 | 72 | 48 |
| | 70% | 1.28 | 304 | 222 | 144 |
| 80% | 30% | 2.67 | 70 | 54 | 36 |
| | 50% | 1.60 | 190 | 126 | 90 |
| | 70% | 1.14 | 1408 | 1008 | 626 |

Based on the above, it is believed that an adequate number of patients could be equal to 126, in a study in which the following is assumed:

Statistics and Methodology

During the process, it became apparent that dropouts and incomplete diary documentation resulted in missing data that could not be adequately handled by the expected robust comparison. To manage the missing data structure, a negative binomial was used, i.e. a generalized linear mixed effects model (NB GLMM) which not only provides unbiased parameter estimates in case of missing random data, "Missing at Random" (MAR), but also provides reasonably stable results when the MAR intake is violated. Patients who did not provide any diary data (leading to zero evaluable days) were excluded from the MAR based primary efficacy analysis, according to an "all observed data approach", as proposed by White and colleagues. This approach is statistically efficient without using multiple imputation techniques. Data retrieved after withdrawal of randomized study treatment were also included in the analysis. Unless otherwise indicated, all experimental results were expressed as the average±standard deviation (SD) of at least three replicates.

Statistical analysis of the data was performed by Student's t-test or two-way ANOVA, followed by Tukey-Kramer multiple comparison test to evaluate significant differences between a pair of media. Statistical heterogeneity was assessed using the Cochran test ($p<0.1$). The I2 statistic was also calculated, and I2>50% was considered as significant heterogeneity between studies. If significant heterogeneity between studies was demonstrated, a random-effects model was used. If not, the results were obtained from a fixed-effects model.

Percent change in the average and SD values was excluded when determining SD values for a result. If not available directly, SD values were calculated from standard errors, 95% CI, p-value, or t-value. Subgroup analyses, defined above, were performed to examine possible sources of heterogeneity within these studies and included health status, study design, type of intervention, duration, total dose, and Jadad score. Treatment effects were analyzed using PROC MIXED with treatment and period as fixed factors, subjects as random factors and baseline measurements as covariates and defined as weighted mean differences and 95% CI, and calculated for net changes in the evaluated parameters. Data that could not satisfy the criteria of homogeneity of variance (Levene's test) and normal distribution (as determined by the examination of the residual diagram and Shapiro-Wilks test) even after the logarithmic transformation, were analyzed by a non-parametric test (Friedman). The significance level (a value) was of 95% in all cases ($P<0.05$).

Analysis Set

The entire analysis set group included all randomized patients and patients who did not fail to meet any important entry criteria. Patients who did not provide primary efficacy data from efficacy analyses were excluded. The protocol set consisted of all patients who did not substantially deviate from the protocol and they exhibited two characteristics: first, this group included patients for whom no major protocol violations were detected (e.g., poor compliance, errors in the assignment of treatment); second, they had to be treated for at least 50 days, starting on the day of the first intake (completion of a certain pre-specified minimum exposure to the treatment regimen). Therefore, patients who discontinued the study or treatment prematurely were excluded from the per-protocol sample.

Results

As can be seen from the data shown in Table 1, the formulation named mix1, consisting in the treatment of subjects belonging to Group 5, and comprising the mixture (mix1) of the three freeze-drieds in equal ratios (1:1:1), favored a decrease in body weight (BW), body mass index (BMI), fat mass (FM), and an increase in lean mass (FFM), greater than the sum of the effects of the components taken individually.

This formulation clearly indicates a synergistic effect of the various constituents of the composition.

The formulation named mix2, consisting in the treatment of subjects belonging to Group 7, and including the mixture (mix2) of the four components in a ratio of (1:1:1:0.15) led to results similar to those observed for mix1. The addition of *griffonia* seeds extract in mix2 therefore does not alter the synergistic effect observed for mix1.

CONCLUSIONS

The nutraceutical product based on a mixture of *cinchona* cortex freeze-dried, gentian root freeze-dried and chicory leaves and roots freeze-dried, in equal ratios (1:1:1), or based on a mixture of *cinchona* cortex freeze-dried, gentian root freeze-dried and chicory leaves and roots freeze-dried, and *griffonia* seeds extract in a ratio of (1:1:1:0.15), is provided as a useful support, or even a possible alternative, to classical pharmacotherapy for body weight loss and body composition control. The results obtained indicate the possibility of an innovative treatment that may represent a valid alternative for the treatment of obesity and associated metabolic diseases in the clinical practice.

TABLE 1

| | | Parameters | | | |
|---|---|---|---|---|---|
| | | BW (kg) | BMI (kg/m$^2$) | FM (%) | FFM (%) |
| Group 1 | T0 | 97.8 ± 1.2 | 36.7 ± 0.4 | 41.5 ± 1.0 | 58.5 ± 0.9 |
| (placebo) | T1 | 93.0 ± 0.9 | 34.9 ± 0.3 | 39.7 ± 0.4 | 60.3 ± 0.3 |
| | Δ% | −4.9 | −4.9 | −4.3 | +3.1 |
| Group 2 | T0 | 94.8 ± 1.1 | 38.2 ± 1.0 | 37.9 ± 0.9 | 62.1 ± 0.7 |
| (chincona) | T1 | 79.8 ± 1.2 | 32.1 ± 1.0 | 27.9 ± 1.7 | 72.1 ± 1.0 |
| | Δ% | −15.8 | −15.7 | −26.5 | +16.2 |
| Group 3 | T0 | 102.8 ± 1.4 | 37.9 ± 0.3 | 44.1 ± 0.6 | 56.2 ± 0.5 |
| (gentian) | T1 | 92.0 ± 1.5 | 34.0 ± 0.4 | 35.1 ± 0.6 | 62.7 ± 0.5 |
| | Δ% | −10.5 | −10.2 | −20.2 | +11.6 |
| Group 4 | T0 | 98.1 ± 1.4 | 38.9 ± 0.3 | 39.3 ± 0.6 | 60.1 ± 0.5 |
| (chicory) | T1 | 91.0 ± 1.2 | 35.9 ± 0.4 | 33.3 ± 1.0 | 64.4 ± 0.9 |
| | Δ% | −7.2 | −7.6 | −15.3 | +7.2 |
| Group 5 | T0 | 100.1 ± 1.2 | 37.4 ± 1.0 | 40.4 ± 1.7 | 57.5 ± 1.0 |
| (mix1) | T1 | 84.3 ± 1.1 | 31.5 ± 1.0 | 30.0 ± 0.9 | 67.8 ± 0.7 |
| | Δ% | −18 | −17.9 | −28.2 | +17.9 |
| Group 6 | T0 | 97.8 ± 1.3 | 37.5 ± 0.4 | 38.2 ± 0.5 | 61.7 ± 0.4 |
| (griffonia) | T1 | 91.9 ± 1.1 | 35.3 ± 0.3 | 34.1 ± 1.1 | 65.8 ± 0.7 |
| | Δ% | −6.0 | −5.9 | −10.7 | +6.5 |
| Group 7 | T0 | 98.9 ± 1.3 | 38.3 ± 1.1 | 39.2 ± 1.5 | 58.3 ± 1.1 |
| (mix2) | T1 | 81.8 ± 1.2 | 31.4 ± 1.0 | 28.0 ± 0.7 | 68.5 ± 0.7 |
| | Δ% | −17.3 | −18.0 | −28.5 | +17.5 |

Group 1: treatment with placebo; Group 2: treatment with chincona cortex freeze-dried; Group 3: treatment with gentian root freeze-dried; Group 4: treatment with chicory leaves and roots freeze-dried; Group 5: treatment with the mixture of three freeze-drieds; Group 6: treatment with griffonia seeds extract; Group 7: treatment with the mixture of the four samples; T0, baseline state; T2, after 60 days of treatment; BW, body weight (kg); BMI, body mass index (kg/m$^2$); FM, fat mass (%); FFM, lean mass (%). Data are expressed as average ± standard deviation.

*p < 0.05

The invention claimed is:

1. A gastro-resistant pharmaceutical or nutraceutical composition comprising:

a. *cinchona* cortex freeze-dried;

b. chicory leaves and roots freeze-dried; and c. gentian root freeze-dried.

2. The composition according to claim 1 further comprising *Griffonia* seeds extract.

3. The composition according to claim 1, wherein the *cinchona* is *Cinchona succirubra* and its cortex freeze-dried contains 1-3% by weight of quinine.

4. The composition according to claim 1, wherein the chicory is *Cichorium intybus*, or *Cichorium endivia*, or *Cichorium pumilum*, or *Cichorium spinosum* and its leaves and roots freeze-dried contains at most 350 mg/kg of lactucin.

5. The composition according to claim 1, wherein the gentian is *Gentiana lutea* and its root freeze-dried contains 1-2% by weight of gentiopicrin.

6. The composition according to claim 2, wherein the *Griffonia* is *Griffonia simplicifolia* and its seed extract contains 98% by weight of 5-HTP.

7. The composition according to claim 1 comprising

| | | |
|---|---|---|
| a. | Chincona cortex freeze-dried | 25-40%; |
| b. | Chicory leaves and roots freeze-dried | 25-40%; |
| c. | gentian root freeze-dried | 25-40%; |

where the percentages indicated are expressed by weight calculated with respect to the total weight of the composition.

8. The composition according to claim 1, wherein the components are contained in a weight ratio of 1:1:1.

9. The composition according to claim 1, formulated as gastro-resistant capsules or tablets.

10. A method of treatment of obesity and associated dysmetabolic diseases, said method comprising administering to a subject in need thereof a composition according to claim 1.

11. A method of appetite control and/or mealtime energy intake reduction or body weight loss said method comprising administering to a subject in need thereof a composition according to claim 1.

12. The composition according to claim 7, comprising

| | | |
|---|---|---|
| a. | Chincona cortex freeze-dried | 30-35%; |
| b. | Chicory leaves and roots freeze-dried | 30-35%; |
| c. | gentian root freeze-dried | 30-35%; |

where the percentages indicated are expressed by weight calculated with respect to the total weight of the composition.

13. The composition according to claim 2, wherein the components are contained in a weight ratio of 1:1:1:0.15.

14. The composition according to claim 2, comprising

| | | |
|---|---|---|
| a. | Chincona cortex freeze-dried | 25-40%; |
| b. | Chicory leaves and roots freeze-dried | 25-40%; |
| c. | gentian root freeze-dried | 25-40%; |
| d. | griffonia seeds extract | 2-15%; |

where the percentages indicated are expressed by weight calculated with respect to the total weight of the composition.

15. The composition according to claim 12, comprising

| | | |
|---|---|---|
| a. | Chincona cortex freeze-dried | 30-35%; |
| b. | Chicory leaves and roots freeze-dried | 30-35%; |
| c. | gentian root freeze-dried | 30-35%; |
| d. | griffonia seeds extract | 5-10%; |

where the percentages indicated are expressed by weight calculated with respect to the total weight of the composition.

* * * * *